(12) United States Patent
Iwakata et al.

(10) Patent No.: US 12,023,198 B2
(45) Date of Patent: Jul. 2, 2024

(54) ULTRASONIC TRANSDUCER ELEMENT, ULTRASONIC PROBE, AND ELECTRODE STRUCTURE OF ULTRASONIC TRANSDUCER ELEMENT

(71) Applicant: CANON MEDICAL SYSTEMS CORPORATION, Otawara (JP)

(72) Inventors: Masahide Iwakata, Ota-ku (JP); Junri Ishikura, Ota-ku (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 629 days.

(21) Appl. No.: 17/333,438

(22) Filed: May 28, 2021

(65) Prior Publication Data
US 2022/0000453 A1 Jan. 6, 2022

(30) Foreign Application Priority Data
May 29, 2020 (JP) ................................ 2020-094975

(51) Int. Cl.
*A61B 8/00* (2006.01)
*A61B 8/08* (2006.01)
*B06B 1/06* (2006.01)

(52) U.S. Cl.
CPC ............ *A61B 8/4494* (2013.01); *A61B 8/488* (2013.01); *B06B 1/064* (2013.01)

(58) Field of Classification Search
CPC ..... A61B 8/4494; A61B 8/488; A61B 8/4483; A61B 8/5246; B06B 1/064
See application file for complete search history.

(56) References Cited

U.S. PATENT DOCUMENTS

| | | | | |
|---|---|---|---|---|
| 5,974,884 | A * | 11/1999 | Sano | .................. G01N 29/2462 73/629 |
| 2013/0090561 | A1* | 4/2013 | Kusukame | ........... A61B 8/4444 977/773 |

FOREIGN PATENT DOCUMENTS

JP 6023581 B2 11/2016

* cited by examiner

*Primary Examiner* — Emily P Pham
(74) *Attorney, Agent, or Firm* — Oblon, McClelland, Maier & Neustadt, L.L.P.

(57) ABSTRACT

An ultrasonic transducer element according to an embodiment includes a plurality of layers including a piezoelectric element layer. At least one surface of electrodes that forms a pair of adjacent layers among the plurality of layers is made of metal including a plurality of needle-like structures, the pair of adjacent layers being made of conductive material and facing each other.

12 Claims, 7 Drawing Sheets

ULTRASONIC TRANSDUCER ELEMENT, ULTRASONIC PROBE, AND ELECTRODE STRUCTURE OF ULTRASONIC TRANSDUCER ELEMENT

CROSS-REFERENCE TO RELATED APPLICATIONS

This application is based upon and claims the benefit of priority from Japanese Patent Application No. 2020-094975, filed on May 29, 2020; the entire contents of which are incorporated herein by reference.

FIELD

Embodiments described herein relate generally to an ultrasonic transducer element, an ultrasonic probe, and an electrode structure of an ultrasonic transducer element.

BACKGROUND

In an ultrasonic probe, it is desirable to make elements constituting an ultrasonic transducer element, particularly piezoelectric elements, smaller, in order to enhance image quality. In addition, in order to improve frequency characteristics of the ultrasonic probe, it is desirable that surfaces of the piezoelectric elements be smoothed.

However, in a case in which the piezoelectric elements are small and smoothed, if the adhesive strength between individual layers of the ultrasonic transducer element is insufficient, the elements may collapse at a dicing step, for example.

In the case in which the piezoelectric elements are small and smoothed, the conductivity between the individual layers of the ultrasonic transducer element may be insufficient, resulting in an electrical conduction failure. Therefore, for example, it is conceivable that a conductive filler is inserted between the individual layers to prevent the electrical conduction failure. However, in this case, the film thickness of an adhesive layer increases, and the frequency characteristics of the ultrasonic probe deteriorate. Therefore, it is desirable that the conductivity between the individual layers of the ultrasonic transducer element is ensured even in a state in which the conductive filler is not introduced.

DETAILED DESCRIPTION

An ultrasonic transducer element according to an embodiment includes a plurality of layers including a piezoelectric element layer. At least one surface of electrodes that forms a pair of adjacent layers among the plurality of layers is made of metal including a plurality of needle-like structures, the pair of adjacent layers being made of a conductive material and facing each other.

Hereinafter, an embodiment of an ultrasonic transducer element, an ultrasonic probe, and an electrode structure of the ultrasonic transducer element will be described in detail with reference to the drawings.

First, an overall configuration of an ultrasonic diagnostic apparatus including an ultrasonic probe according to an embodiment will be described with reference to FIG. 1.

Figure 1:
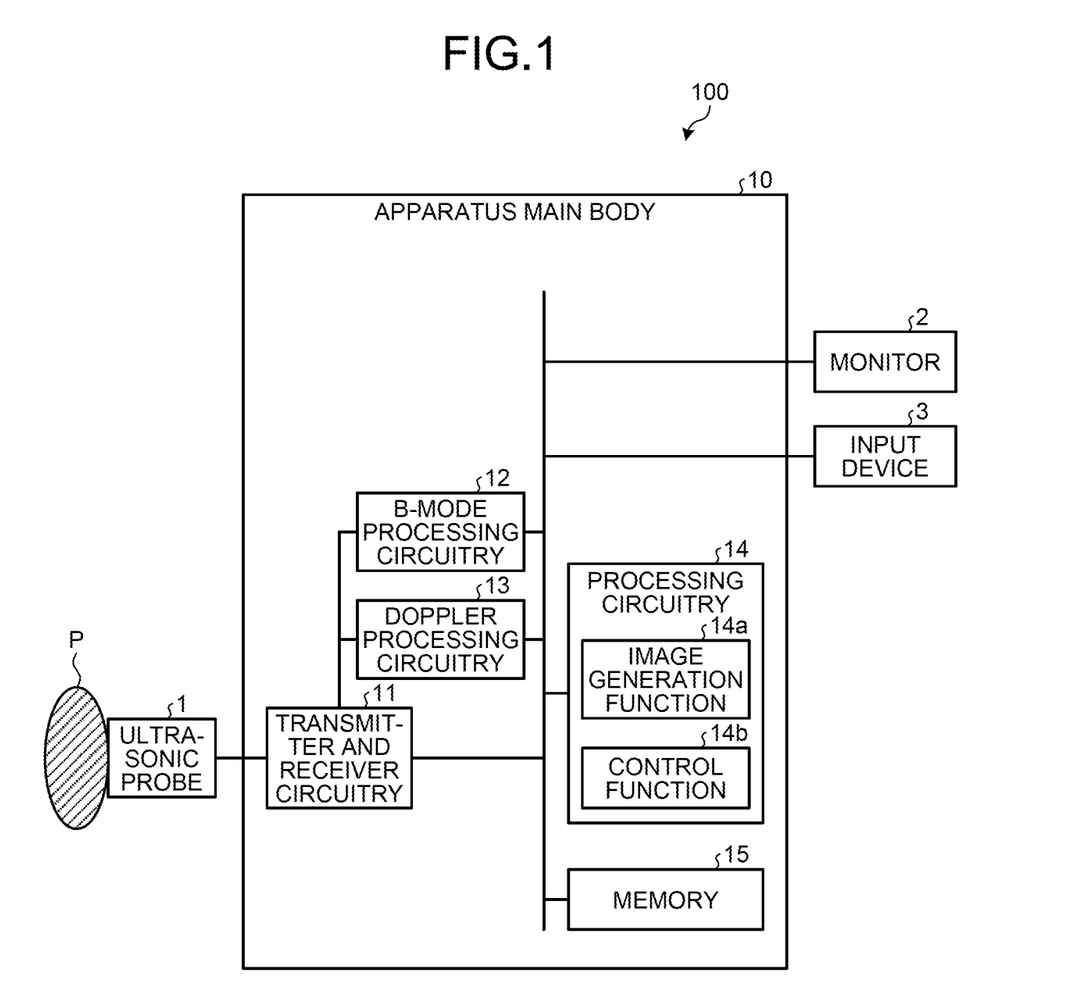
FIG. 1 is a diagram illustrating a configuration of an ultrasonic diagnostic apparatus according to an embodiment.

As illustrated in FIG. 1, an ultrasonic diagnostic apparatus 100 according to the embodiment includes an ultrasonic probe 1, a monitor 2, an input device 3, and an apparatus main body 10.

The ultrasonic probe 1 includes an ultrasonic transducer element unit that transmits ultrasonic waves and receives reflected-waves. The ultrasonic transducer element unit includes a plurality of ultrasonic transducer elements. Each of the ultrasonic transducer elements includes a piezoelectric element, and the piezoelectric element generates ultrasonic waves based on a drive signal supplied from transmitter and receiver circuitry 11 included in the apparatus main body 10 described later. The piezoelectric element of each of the ultrasonic transducer elements receives reflected-waves from a subject P and converts the received reflected-waves into electric signals. As described later, each of the ultrasonic transducer elements included in the ultrasonic transducer element unit includes an acoustic matching layer provided to the piezoelectric element and a back load material (back matching layer) that suppresses propagation of ultrasonic waves from the piezoelectric element toward the back. The ultrasonic probe 1 is connected to the apparatus main body 10 in an attachable and detachable manner.

For example, when ultrasonic waves are transmitted from the ultrasonic probe 1 to the subject P, the transmitted ultrasonic waves are sequentially reflected by a surface of discontinuity of acoustic impedance in a body tissue of the subject P, and the ultrasonic waves are then received by the ultrasonic transducer elements of the ultrasonic probe 1 as reflected-waves. The reflected-waves are converted into reflected-wave signals that are electric signals by the piezoelectric element of the ultrasonic transducer element that has received the reflected-waves. The amplitude of the reflected-wave signals depends on the difference in the acoustic impedance on the surface of discontinuity on which the ultrasonic waves are reflected. The reflected-wave signals may be obtained by the transmitted ultrasonic pulses being reflected by moving bloodstream or a surface of a cardiac wall and the like, and in this case, the reflected-wave signals are frequency-shifted by Doppler effect depending on a velocity component of a moving body in an ultrasonic-wave transmission direction.

The monitor 2 displays a graphical user interface (GUI) for an operator of the ultrasonic diagnostic apparatus 100 to input various setting requests using the input device 3, or displays an ultrasonic image or the like generated by the apparatus main body 10.

The input device 3 includes a trackball, a switch, a dial, a touch command screen, and the like. The input device 3 receives the various setting requests from the operator of the ultrasonic diagnostic apparatus 100, and transfers the received various setting requests to the apparatus main body 10. For example, the input device 3 receives various setting requests for controlling the ultrasonic probe 1 and transfers the various setting requests to processing circuitry 14.

The apparatus main body 10 is a device that controls transmission and reception of ultrasonic waves by the ultrasonic probe 1 and generates an ultrasonic image based on the reflected-waves received by the ultrasonic probe 1. As illustrated in FIG. 1, the apparatus main body 10 includes the transmitter and receiver circuitry 11, B-mode processing circuitry 12, Doppler processing circuitry 13, processing circuitry 14, and a memory 15.

The transmitter and receiver circuitry 11 includes trigger generating circuitry, delay circuitry, pulser circuitry, and the like, and supplies drive signals to the ultrasonic probe 1. The pulser circuitry repeatedly generates a rate pulse to form transmission ultrasonic waves at a predetermined rate frequency. The delay circuitry supplies delay time for each ultrasonic transducer element to each rate pulse generated by the pulser circuitry, in which the delay time is required to collimate the ultrasonic waves generated from the ultrasonic probe 1 in a beam-shape and determine the transmission directionality. The trigger generating circuitry supplies drive signals (drive pulse) to the ultrasonic probe 1 at a timing based on the rate pulse. That is, the delay circuitry changes the delay time supplied to each rate pulse so as to adjust the transmission direction from a surface of the ultrasonic transducer element as desired.

The transmitter and receiver circuitry 11 has a function of instantaneously changing a transmission frequency, a transmission drive voltage, and the like in order to execute a predetermined scan sequence, based on an instruction of a control function 14b of the processing circuitry 14 described later. In particular, the configuration to change the transmission drive voltage is implemented by using linear-amplifier-type transmitting circuitry that has a value capable of being instantly switched or by using a mechanism that electrically switches between a plurality of power source units.

The transmitter and receiver circuitry 11 includes amplifying circuitry, an analog/digital (A/D) converter, an adder, and the like and generates reflected-wave data by performing various pieces of processing on the reflected-wave signals received by the ultrasonic probe 1. The amplifying circuitry performs gain correction processing by amplifying the reflected-wave signals for each of channels. The A/D converter performs an A/D conversion of the gain-corrected reflected-wave signal and applies a delay time required to determine reception directionality to digital data. The adder performs addition processing on the reflected-wave signal processed by the A/D converter so as to generate reflected-wave data. As a result of the addition processing performed by the adder, reflected components from the direction corresponding to the reception directionality of the reflected-wave signal are emphasized. In this manner, the transmitter and receiver circuitry 11 controls the transmission directionality and the reception directionality in the transmission and the reception of the ultrasonic waves.

The B-mode processing circuitry 12 receives the reflected-wave data from the transmitter and receiver circuitry 11 and generates data (B-mode data) in which the strength of each signal is expressed by a degree of brightness, by performing a logarithmic amplification, an envelope detection process, and the like on the received reflected-wave data.

The Doppler processing circuitry 13 obtains velocity information from the reflected-wave data received from the transmitter and receiver circuitry 11 by performing a frequency analysis to extract bloodstream, tissues, and contrast-agent echo components under the influence of the Doppler effect, and further generates data ("Doppler data") obtained by extracting moving body information such as an average velocity, dispersion, a power, and the like, for a plurality of points.

The processing circuitry 14 includes, for example, a control processor (central processing unit (CPU)) that provides a function as an information processing device (computer).

With an image generation function 14a, the processing circuitry 14 generates an ultrasonic image from pieces of data generated by the B-mode processing circuitry 12 and the Doppler processing circuitry 13. That is, with an image generation function 14a, the processing circuitry 14 generates a B-mode image in which intensity of the reflected-waves is expressed by brightness from the B-mode data generated by the B-mode processing circuitry 12.

In addition, with the image generation function 14a, the processing circuitry 14 generates a color Doppler image as an average velocity image, a variance image, a power image, or a combination image thereof indicating moving body information from the Doppler data generated by the Doppler processing circuitry 13.

With the control function 14b, the processing circuitry 14 controls pieces of processing by the transmitter and receiver circuitry 11, the B-mode processing circuitry 12, the Doppler processing circuitry 13, and the like based on various setting requests input from the operator through the input device 3 and various control programs and various pieces of data loaded from the memory 15. The processing circuitry 14 controls the monitor 2 to display the ultrasonic image and various images stored in the memory 15, the GUI for performing various pieces of processing, processing results by the image generation function 14a, or the like with the control function 14b.

The memory 15 is a memory that stores the ultrasonic image generated by the processing circuitry 14 using the image generation function 14a. The memory 15 can also store pieces of data generated by the B-mode processing circuitry 12 and the Doppler processing circuitry 13.

The memory 15 stores various pieces of data such as control programs for performing transmission and reception of ultrasonic waves, image processing, and display processing, diagnosis information (for example, patient IDs and findings by physicians), diagnostic protocols, and various types of body marks.

Figure 2:
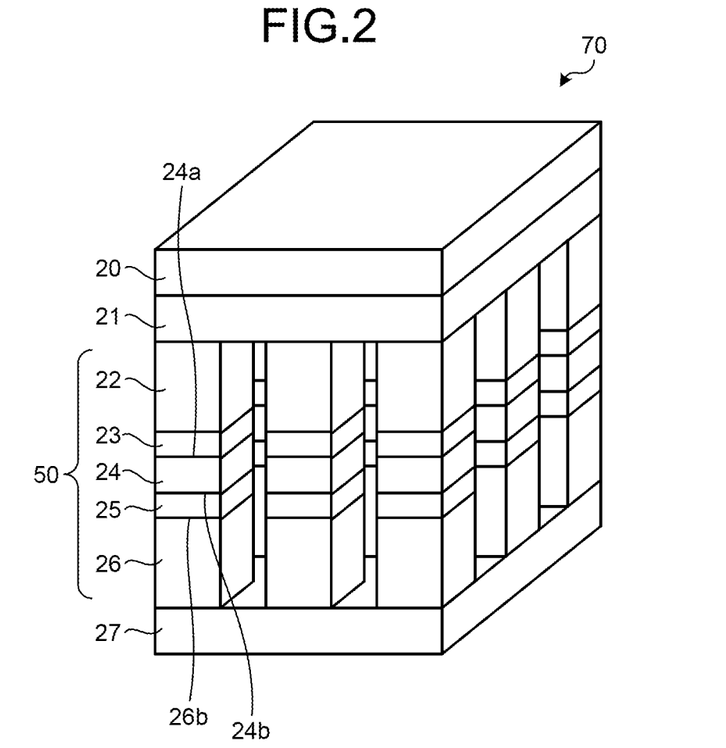
FIG. 2 is a diagram illustrating an ultrasonic transducer element according to the embodiment.

Next, an example of the configuration of the ultrasonic transducer element unit included in the ultrasonic probe 1 according to the embodiment will be described with reference to FIGS. 2 to 5. FIG. 2 is an oblique projection view of an example of an ultrasonic transducer element unit 70 included in the ultrasonic probe 1 according to the embodiment.

Hereinbelow, the term "layer" means an individual layer in a laminated structure if being used for the laminated structure before dicing processing, and means an individual layer in each of a plurality of ultrasonic transducer elements if being used for the ultrasonic transducer elements after dicing processing.

The ultrasonic transducer element unit 70 is built in the ultrasonic probe 1, and performs transmission and reception of ultrasonic waves on a living body with which the probe comes into contact. The ultrasonic transducer element unit 70 includes, for example, a plurality of ultrasonic transducer elements 50 arranged two-dimensionally, and flexible printed circuits (FPCs) 21 and 27 on which the ultrasonic transducer elements 50 are disposed, and an acoustic lens 20. Each of the ultrasonic transducer elements 50 includes, for example, a piezoelectric element 24, an acoustic matching layer 22, and a back matching layer 26.

An adhesive layer 23 between the piezoelectric element 24 and the acoustic matching layer 22 and an adhesive layer 25 between the piezoelectric element 24 and the back matching layer 26 are filled with an adhesive. As the adhesive to be filled between the piezoelectric element 24 and the acoustic matching layer 22, for example, a non-conductive adhesive having a low-viscosity, such as an epoxy-based adhesive may be used.

The adhesive to be filled between the piezoelectric element 24 and the back matching layer 26 may be a non-conductive adhesive or a conductive adhesive.

For example, an electrode film is formed on a surface of each of the layers. For example, an electrode film of a signal electrode 24a, an electrode film of a ground electrode 24b, and the like are formed on both surfaces of the piezoelectric element 24. Similarly, an electrode film 26b is formed on a surface of the back matching layer 26, for example, a surface of the back matching layer 26 on the piezoelectric element 24 side, and an electrode film is also formed on a surface of the acoustic matching layer 22, for example, a surface of the acoustic matching layer 22 on the piezoelectric element 24 side.

These electrode films are made of gold, silver, nickel, or other metals with good conductivity. Furthermore, as a method for forming these electrode layers, plating, vapor deposition, ion plating, sputtering, baking, chemical vapor deposition (CVD), and the like can be adopted.

The piezoelectric element 24 is an element having piezoelectricity. For example, the piezoelectric element 24 is a piezoelectric element including PZT (lead zirconate titanate/Pb(Zr,Ti)O$_3$), PMN-PT (lead magnesium niobate-lead titanate/Pb(Mg$_{1/2}$Nb$_{2/3}$)O$_3$—PbTiO$_3$), or the like. In the embodiment, the ultrasonic transducer elements 50 are arranged and provided on a predetermined surface of the flexible printed circuitry 27. The signal electrode 24a is provided on a surface (ultrasonic radiation surface) of the piezoelectric element 24 from which the ultrasonic waves are radiated. The ground electrode 24b is provided on a surface (back surface) of the piezoelectric element 24 that is the opposite side to the ultrasonic radiation surface.

The piezoelectric element 24 is driven by a drive signal from the transmitter and receiver circuitry 11 to radiate ultrasonic waves from the surface on the signal electrode 24a side. When the piezoelectric element 24 receives reflected-waves, the piezoelectric element 24 converts the received reflected-waves into reflected-wave signals, and outputs the converted reflected-wave signals from the signal electrode 24a.

The acoustic matching layer 22 is a layer for gradually reducing the acoustic impedance from the piezoelectric element 24 to the living body to acoustically match the piezoelectric element 24 with the living body. The acoustic matching layer 22 may be formed of only one layer, or may include a plurality of layers in order to reduce the acoustic impedance toward the living body as smoothly as possible. As the acoustic matching layer 22, for example, a resin mixed with carbon, graphite material, or a conductive filler can be used in order to have conductivity. As this resin, an epoxy resin can be used, for example.

The back matching layer 26 is made of a material having higher acoustic impedance than that of the piezoelectric element 24, and as a resonance layer, the back matching layer 26 is integrated with the piezoelectric element 24 to perform transmission and reception of ultrasonic waves.

The flexible printed circuits 21 and 27 are flexible printed circuits (FPCs), and allows the signal electrode 24a and the ground electrode 24b to be electrically connected to the transmitter and receiver circuitry 11 through wires provided in the individual layers of each ultrasonic transducer element 50.

The acoustic lens 20 collimates ultrasonic waves. The acoustic lens 20 is provided on a surface of the flexible printed circuitry 21 to which ultrasonic waves are radiated.

Figure 3:
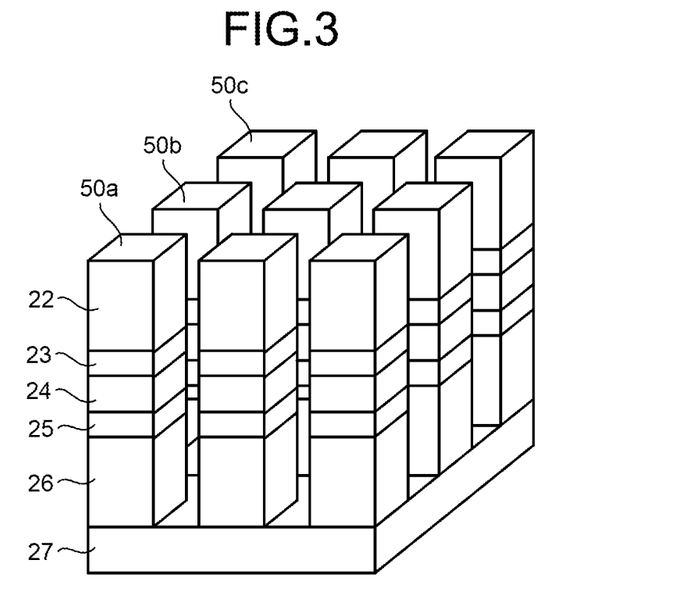
FIG. 3 is a diagram illustrating manufacture of the ultrasonic transducer element according to the embodiment.

The appearance of the ultrasonic transducer element unit 70 in a state in which the acoustic lens 20 and the flexible printed circuitry 21 are removed from the state of FIG. 2 is illustrated in FIG. 3. In FIG. 3, ultrasonic transducer elements 50a, 50b, and 50c illustrate each ultrasonic transducer element in which the acoustic matching layer 22, the back matching layer 26, and the like are laminated on the layer of the piezoelectric element 24.

Figure 4:
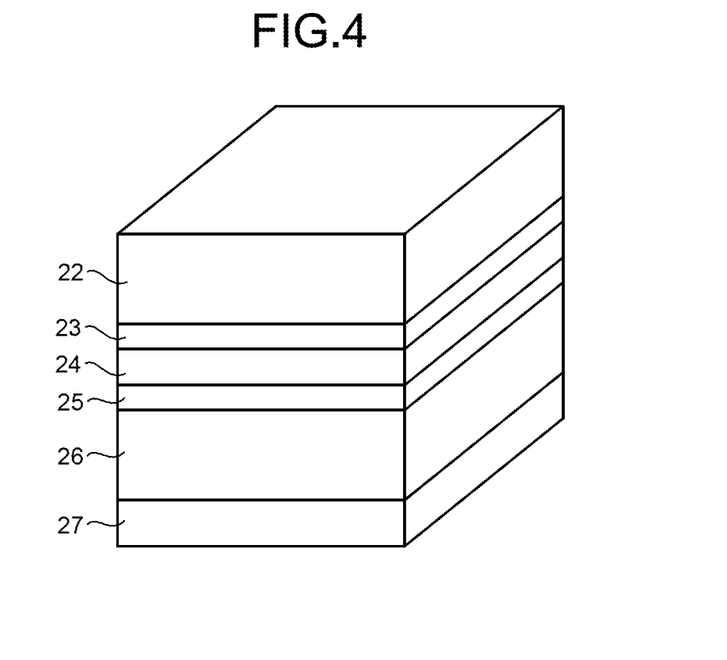
FIG. 4 is a diagram illustrating the manufacture of the ultrasonic transducer element according to the embodiment.

These ultrasonic transducer elements 50a, 50b, and 50c are obtained such that a laminated structure before dicing processing, which is illustrated in FIG. 4, is vertically and horizontally cut with a cutting tool such as a dicing saw, and each of the ultrasonic transducer elements 50a, 50b, 50c, and the like are formed by cutting out, for example, into an array having a two-dimensional arrangement.

Next, an electrode structure of each of the ultrasonic transducer elements 50 of the ultrasonic transducer element unit 70 according to the embodiment will be described with reference to FIG. 5.

Specifically, each of the ultrasonic transducer elements 50 according to the embodiment includes a plurality of layers including a piezoelectric element layer (a layer of the piezoelectric element 24), and at least one surface of electrodes that form a pair of adjacent layers among the layers, are made of a conductive material, and face each other is made of metal including a plurality of needle-like structures.

That is, in the electrode structure of each ultrasonic transducer element 50 according to the embodiment, at least one surface of surfaces that forms a pair of adjacent layers among the layers is provided with an electrode made of metal including a plurality of needle-like structures. The pair pf adjacent layers are made of conductive material, and faces each other. Here, the term "at least one surface" means one surface or both surfaces.

The pair of adjacent layers includes, for example, the piezoelectric element layer (the layer of the piezoelectric element 24) and the acoustic matching layer 22. For example, the electrode film (the signal electrode 24a) formed on a surface of the layer of the piezoelectric element 24 and the electrode film formed on a surface of the acoustic matching layer 22 are microscopically adjacent to each other. In such a case, in the embodiment, at least one surface of an electrode film that is made of conductive material and is formed on a surface of the layer of the piezoelectric element 24 and an electrode film that is formed on the acoustic matching layer 22 that faces the electrode film has an electrode made of metal including the needle-like structures.

As another example, the pair of adjacent layers includes, for example, the piezoelectric element layer (the layer of the piezoelectric element 24) and the back matching layer 26. More microscopically, the pair of adjacent layers includes, for example, the electrode film (the ground electrode 24b) formed on a surface of the layer of the piezoelectric element 24 and the electrode film formed on a surface of the back matching layer 26. That is, at least one surface of an electrode film that is made of the conductive material and is formed on a surface of the layer of the piezoelectric element 24 and an electrode film that is formed on the back matching layer 26 that faces the electrode film is provided with an electrode made of metal including the needle-like structures.

As another example, the pair of adjacent layers may include other surfaces. For example, the pair of adjacent layers may include, for example, the flexible printed circuitry 21 and the acoustic matching layer 22, or may include the back matching layer 26 and the flexible printed circuitry 27. For example, in a case in which the acoustic matching layer 22 or the like is formed of a plurality of layers, the pair of adjacent layers may include a pair of adjacent layers out of the plurality of layers.

A case in which the needle-like structures are disposed on one surface of the pair of adjacent layers will be described with reference to FIG. 5. Hereinafter, a layer on which the needle-like structures are disposed is referred to as a first layer, and a layer facing the first layer is referred to as a second layer.

A case in which the layer of piezoelectric element 24 is the first layer on which the needle-like structures are disposed and the acoustic matching layer 22 is the second layer facing the first layer will be described as follows.

Figure 5:
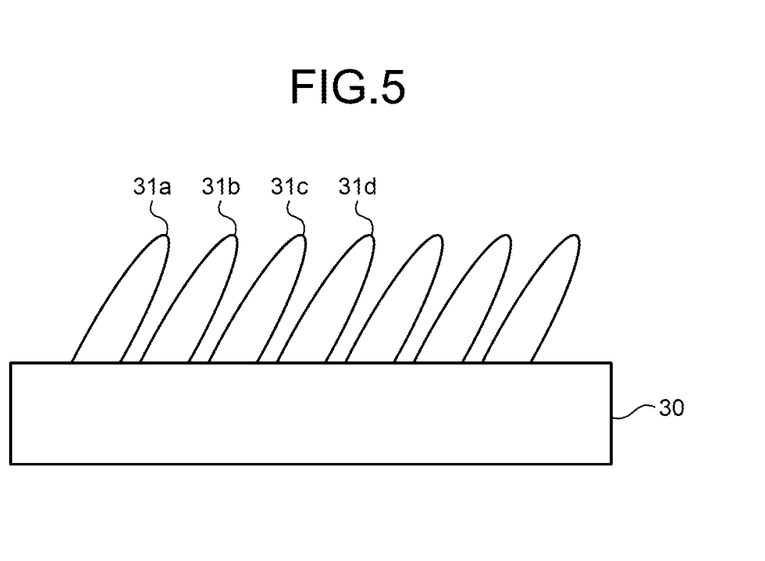
FIG. 5 is a diagram illustrating an electrode structure of the ultrasonic transducer element according to the embodiment.

As illustrated in FIG. 5, a plurality of needle-like structures 31a, 31b, 31c, and 31d are disposed, in such a manner as to be inclined at a constant angle, on a surface of an electrode film 30 formed on a surface of the first layer. In a case in which the first layer is the layer of the piezoelectric element 24, the electrode film of the signal electrode 24a formed on the surface of the layer of the piezoelectric element 24 is the electrode film 30 of FIG. 5, and the needle-like structures 31a, 31b, 31c, and 31d are disposed, in such a manner as to be inclined at a constant angle, on the surface of the electrode film. Non-conductive adhesive such as an epoxy resin-based adhesive is filled between the pair of adjacent layers.

A center average roughness Ra of the electrode film 30 that is the one surface is typically 0.0002 μm or greater and 0.4 μm or smaller. A root mean square slope of the needle-like structures 31a, 31b, 31c, 31d, and the like is typically 2.0 or greater. An average pitch of the needle-like structures 31a, 31b, 31c, 31d, and the like is typically 30 nm or greater and 150 nm or smaller. A developed area ratio of the needle-like structures 31a, 31b, 31c, 31d, and the like, that is, a surface area per unit area is 4 or greater.

In FIG. 5, the case in which the needle-like structures 31a, 31b, 31c, and 31d are disposed, in such a manner as to be inclined at a constant angle, on the surface of the electrode film 30 is described, but the embodiment is not limited thereto, and the needle-like structures may be provided in such a manner as not to be inclined.

Next, with reference to FIG. 6, a method for manufacturing the ultrasonic transducer element unit according to the embodiment will be described focusing on a method for manufacturing a layer including the needle-like structures.

Figure 6:
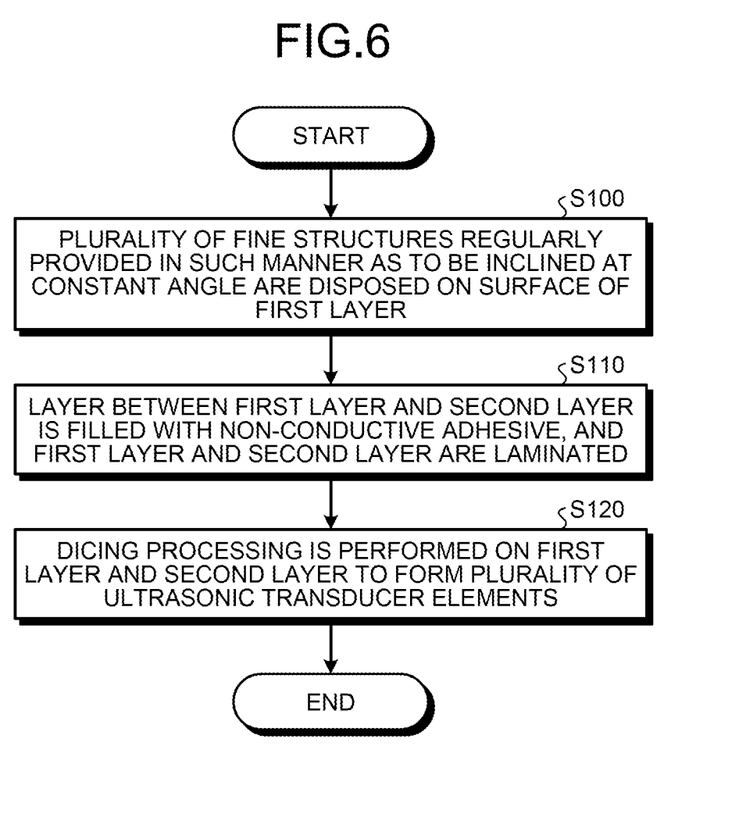
FIG. 6 is a flowchart illustrating a flow of a method for manufacturing the ultrasonic transducer element according to the embodiment.

FIG. 6 is a flowchart illustrating a flow of a method for manufacturing the ultrasonic transducer element according to the embodiment. First, step S100 and step S110, through which the first layer having a surface on which the needle-like structures 31a, 31b, 31c, 31d, and the like are formed and the second layer corresponding to the first layer are laminated, will be described.

First, the electrode film 30 is formed on a surface of the first layer. The electrode film 30 is made of gold, silver, nickel, or other metals with good conductivity. As a method for forming an electrode layer, plating, vapor deposition, ion plating, sputtering, baking, chemical vapor deposition (CVD), and the like can be adopted. Similarly, an electrode film is formed on a surface of the second layer in the same manner.

Subsequently, at step S100, the electrode film 30 on the surface of the first layer is shaped to form, in the surface of the electrode film 30, the needle-like structures 31a, 31b, 31c, and 31d that are regularly provided in such a manner as to be inclined at a constant angle. These needle-like structures 31a, 31b, 31c, and 31d are formed through, for example, electrode film formation by oblique incident deposition or oblique incident sputtering, or microstructure formation by post-processing using a femtosecond laser. For example, in the case of oblique incident film formation, the electrode film 30 and the needle-like structures 31a, 31b, 31c, and 31d can be continuously formed under one condition, whereas in the case of using a femtosecond laser, the needle-like structures are formed by giving the electrode film 30 the shape of needles in post-processing.

The electrode film 30 can be formed of a single layer or a plurality of layers. As metal of the outermost layer of the electrode film 30, gold, silver, or nickel can be adopted. The electrode film 30 can be formed into a plurality of layers in order to improve the adhesion strength between a material constituting a layer and an electrode film. For example, the outermost layer that is a layer adjacent to the layer filled with an adhesive can be gold, and chrome, titanium, or the like can be provided between the outermost layer and a material of the first layer.

In a case in which the needle-like structures are formed on the second layer side, the same processing is performed on the electrode film of the second layer. In this case, a direction and an angle of inclination of the needle-like structures on the first layer may be the same as or different from a direction and an angle of inclination of the needle-like structures on the second layer.

Subsequently, at step S110, a layer between the first layer and the second layer is filled with a non-conductive adhesive such as an epoxy-based adhesive, and the first layer and the second layer are laminated. Specifically, the adhesive is applied between the first layer and the second layer, and after laminating individual layers, the adhesive is cured by a pressing and heating treatment.

The individual layers other than the first layer and the second layer are sequentially laminated according to a general method for manufacturing an ultrasonic transducer element.

Subsequently, when laminating processing of the individual layers of the ultrasonic transducer element unit is completed and the laminated structure before dicing processing is obtained, for example, as illustrated in FIG. 4, the process proceeds to step S120 where a tool such as a dicing saw is used to perform dicing processing and the ultrasonic transducer elements 50a, 50b, 50c, and the like are formed, for example, as illustrated in FIG. 3. Thereafter, these ultrasonic transducer elements are connected to the flexible printed circuitry 21, the acoustic lens 20, and the like, and therefore the ultrasonic transducer element unit 70 as illustrated in FIG. 2 is formed.

Next, the effect of using the configuration according to the embodiment will be described with reference to FIGS. 7 to 10.

Figure 7:
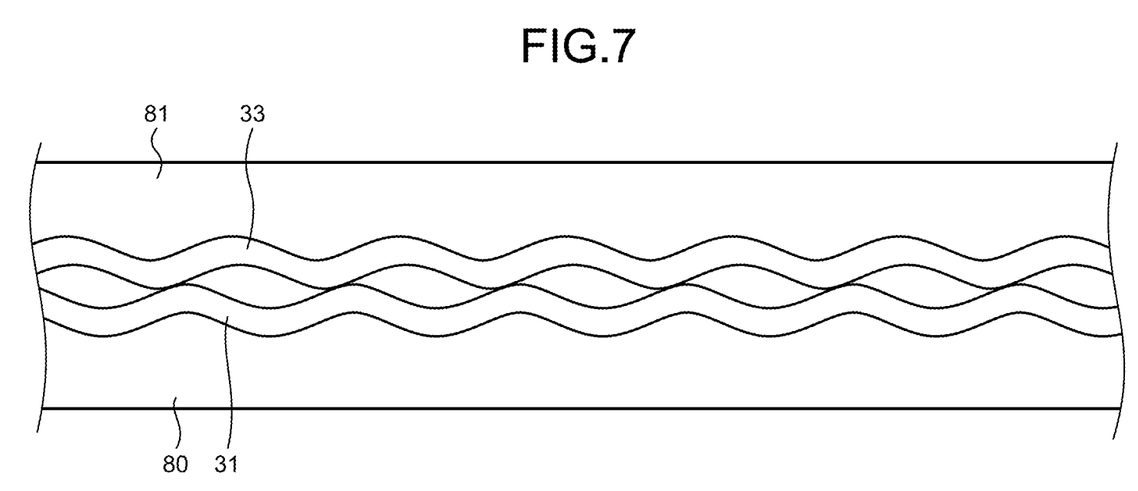
FIG. 7 is a diagram illustrating an electrode structure of an ultrasonic transducer element according to a comparative example.

FIG. 7 is a diagram illustrating an electrode structure of an ultrasonic transducer element according to a comparative example. An example of FIG. 7 illustrates, as the comparative example, a case in which the needle-like structures are not disposed in an electrode film 31 formed on the surface of a first layer 80, and the needle-like structures are also not disposed in an electrode film 33 formed on the surface of a second layer 81 that is a layer adjacent to the first layer 80.

Figure 8:
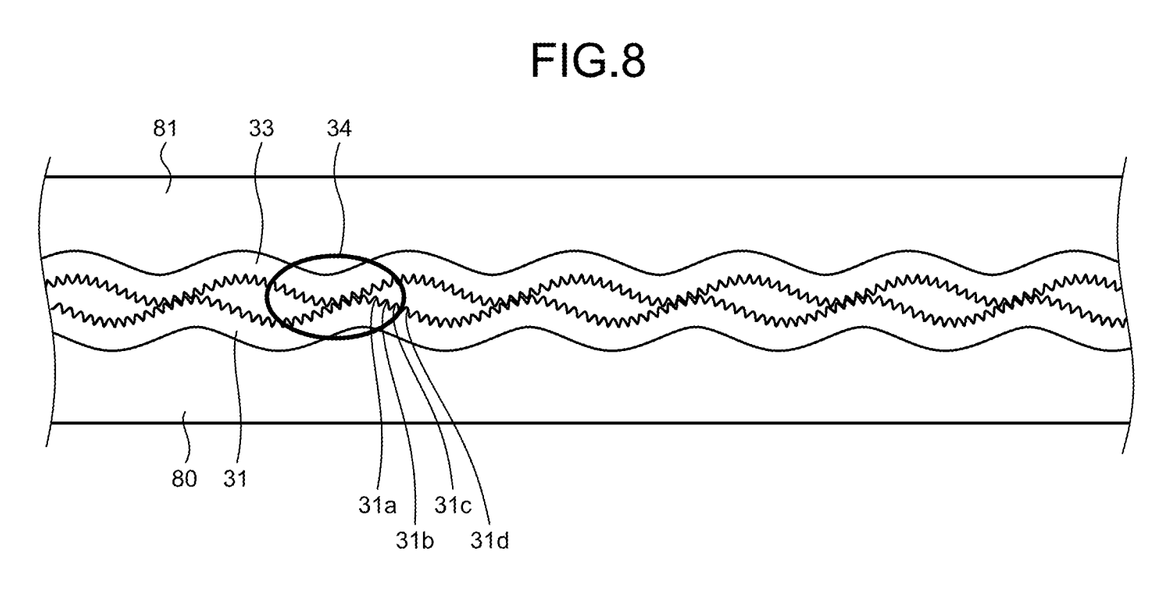
FIG. 8 is a diagram illustrating the electrode structure of the ultrasonic transducer element according to the embodiment.

On the other hand, FIG. 8 is a diagram illustrating the electrode structure of the ultrasonic transducer element according to the embodiment. In an example of FIG. 8, the needle-like structures 31*a*, 31*b*, 31*c*, 31*d*, and the like are disposed in the electrode film 31 formed on the surface of the first layer 80. In addition, the needle-like structures are also disposed in the electrode film 33 formed on the surface of the second layer 81 that is a layer adjacent to the first layer 80.

Figure 9:
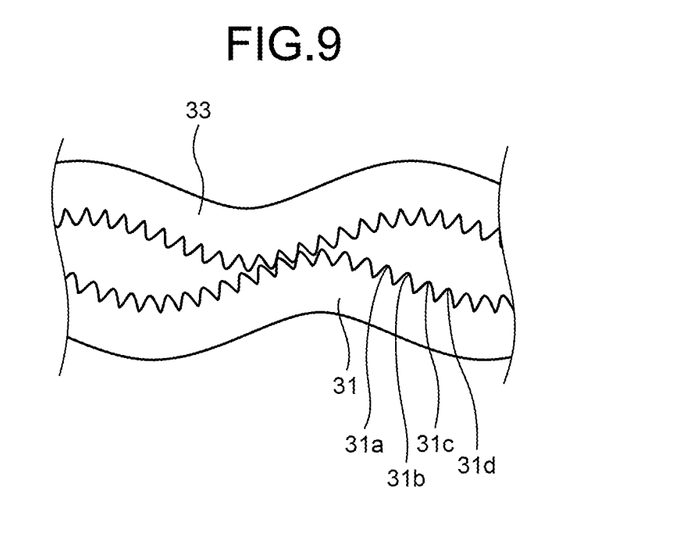
FIG. 9 is an enlarged view illustrating the electrode structure of the ultrasonic transducer element according to the embodiment.

An enlarged view of a region 34 of FIG. 8 is illustrated in FIG. 9.

Next, FIG. 8 illustrating the electrode structure of the ultrasonic transducer element according to the embodiment is compared with FIG. 7 illustrating the electrode structure of the ultrasonic transducer element according to the comparative example.

First, in terms of adhesive strength, as illustrated in FIG. 9, since in the case of the ultrasonic transducer element according to the embodiment, appropriate fine structures are applied to the electrode film 31 and the electrode film 33, the adhesive on recessed parts on the surface is involved in the adhesion between the layers adjacent to each other. That is, for example, an average pitch of the needle-like structures 31*a*, 31*b*, 31*c*, 31*d*, and the like is 30 nm or greater and 150 nm or smaller or a developed area ratio thereof is 4 or greater, so that the anchor effect is generated on the needle-like structures 31*a*, 31*b*, 31*c*, 31*d*, and the like on the surfaces of the electrode films. As a result, the adhesive strength between the first layer 80 and the second layer 81 can be maintained.

In addition, since the needle-like structures 31*a*, 31*b*, 31*c*, 31*d*, and the like are inclined in a predetermined direction, and, for example, a root mean square slope of these needle-like structures 31*a*, 31*b*, 31*c*, and 31*d* is 2.0 or greater, the electrode films can have a large adhesive strength in a peeling direction.

On the other hand, in the case of FIG. 7, the needle-like structures are not disposed in the ultrasonic transducer element, and appropriate fine structures are not applied to the electrode film 31 and the electrode film 33. Therefore, the adhesive strength between the first layer 80 and the second layer 81 is weak.

Secondly, in terms of conductivity, the conductivity improves as the number of contact points between layers increases. Here, as illustrated in the enlarged view of FIG. 9, in a case in which the needle-like structures 31*a*, 31*b*, 31*c*, and 31*d* are disposed in the electrode film 31, the number of contact points between the electrode film 31 and the electrode film 33 increases. Therefore, the conductivity between the first layer 80 and the second layer 81 increases.

Naturally, the conductivity between the first layer 80 and the second layer 81 can be ensured by mixing a conductive filler with the non-conductive adhesive to be filled between the first layer 80 and the second layer 81. However, in the case in which the conductive filler is mixed with the non-conductive adhesive, the thickness of the layer between the first layer 80 and the second layer 81 tends to increase. Therefore, the ultrasonic characteristics may deteriorate.

In the configuration according to the embodiment, because the conduction between the first layer 80 and the second layer 81 can be ensured despite the conductive filler not being mixed in, the conductivity between the first layer 80 and the second layer 81 can be ensured while the thickness of the layer therebetween remains thin, and the frequency characteristics of the ultrasonic transducer element can be maintained in good condition.

On the other hand, in the configuration according to the comparative example as illustrated in FIG. 7, because the number of contact points between the electrode film 31 and the electrode film 33 is small and the contact area is also small, the conductivity between the first layer 80 and the second layer 81 is low.

That is, in the configuration according to the embodiment, the needle-like structures are disposed in the electrode surface, so that the number of contact points between the first layer 80 and the second layer 81 increases even if the center average roughness Ra of the electrode film 31 is the same as in the case in which the needle-like structures are not provided, thereby the conductivity being improved.

In other words, in the configuration according to the embodiment, the center average roughness Ra of the electrode film 31 can be reduced while the conductivity is ensured. In a case in which the center average roughness Ra is large, the frequency characteristic of the ultrasonic transducer element tends to decrease. Therefore, in the configuration according to the embodiment, the conductivity between the first layer 80 and the second layer 81 can be ensured while the frequency characteristics of the ultrasonic transducer element are maintained in good condition.

For example, in the configuration according to the embodiment, since the center average roughness Ra of the electrode film 31 can be set to 0.0002 μm or greater and 0.4 μm or smaller, the frequency characteristics of the ultrasonic transducer element according to the embodiment can be ensured in good condition.

Summarizing the above, in the ultrasonic transducer element according to the embodiment, the adhesive strength and the conductivity between the first layer 80 and the second layer 81 can be ensured while the frequency characteristics are ensured in good condition.

Figure 10:
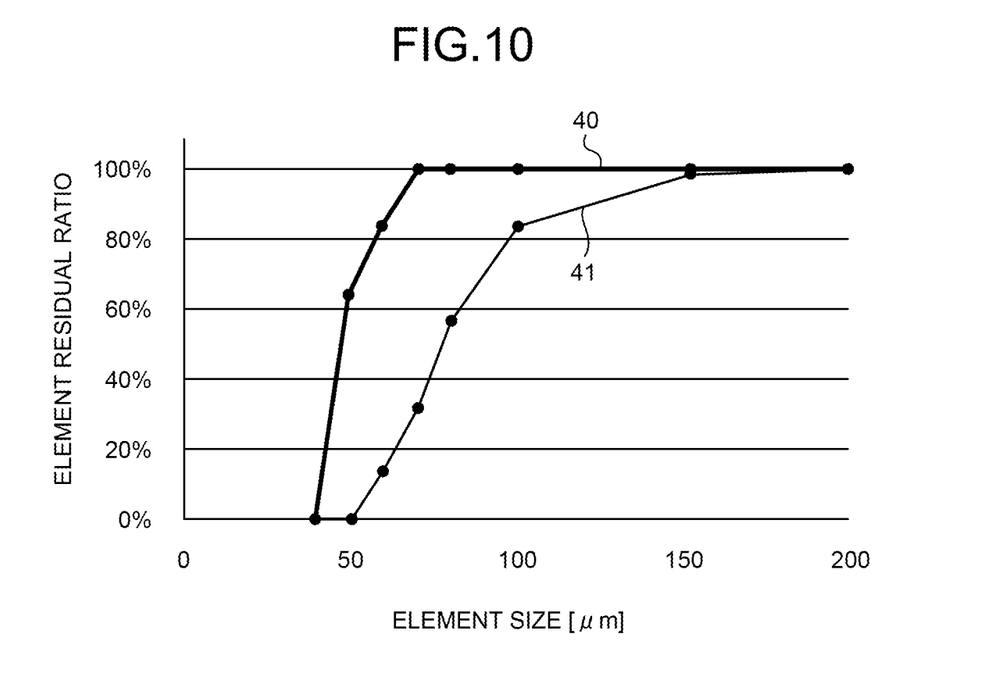
FIG. 10 is a diagram illustrating the ultrasonic transducer element according to the embodiment.

In FIG. 10, an example of the results of experiments conducted to compare the adhesive strength between the ultrasonic transducer element unit 70 according to the embodiment and the ultrasonic transducer element unit according to the comparative example is illustrated. A graph 40 is a graph in which the element residual ratio in the configuration according to the embodiment, that is, the element residual ratio of the ultrasonic transducer element in which the needle-like structures are provided is plotted as a function of the element size. Here, the element residual ratio means the non-defective rate of the ultrasonic transducer element, that is, the ratio of ultrasonic transducer elements other than the ultrasonic transducer elements that collapsed at a step such as dicing, as a result of the adhesive peeling off due to insufficient adhesive strength or the like. On the other hand, a graph 41 is a graph in which the element residual ratio in the configuration according to the comparative example, that is, the element residual ratio of the ultrasonic transducer element in which the needle-like structures are not provided is plotted as a function of the element size.

With reference to the graph 40, the element residual ratio in the configuration according to the embodiment is higher than that in the configuration according to the comparative example, as compared based on the same element size. Therefore, in the configuration according to the embodiment, as compared with the configuration according to the comparative example, the element residual ratio can remain high even if the element size decreases, and thus the element size can be reduced.

According to at least one embodiment described above, both adhesive strength and conductivity can be achieved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic transducer element comprising a plurality of layers including a piezoelectric element layer, wherein
   at least one surface of electrodes that forms a pair of adjacent layers among the plurality of layers is made of metal including a plurality of needle-like structures, the pair of adjacent layers being made of conductive material and facing each other.

2. The ultrasonic transducer element according to claim 1, wherein the needle-like structures are provided in such a manner as to be inclined.

3. The ultrasonic transducer element according to claim 1, wherein non-conductive adhesive is filled between the pair of adjacent layers.

4. The ultrasonic transducer element according to claim 1, wherein a center average roughness of the at least one surface is 0.0002 μm or greater and 0.4 μm or smaller.

5. The ultrasonic transducer element according to claim 1, wherein a root mean square slope of the needle-like structures is 2.0 or greater.

6. The ultrasonic transducer element according to claim 1, wherein an average pitch of the needle-like structures is 30 nm or greater and 150 nm or smaller.

7. The ultrasonic transducer element according to claim 1, wherein a developed area ratio of the needle-like structures is 4 or greater.

8. The ultrasonic transducer element according to claim 1, wherein the pair of adjacent layers includes a piezoelectric element layer and an acoustic matching layer.

9. The ultrasonic transducer element according to claim 1, wherein the pair of adjacent layers includes a piezoelectric element layer and a back matching layer.

10. The ultrasonic transducer element according to claim 1, wherein both surfaces of the electrodes facing each other are made of metal including the needle-like structures.

11. An ultrasonic probe comprising a plurality of ultrasonic transducer elements each including a plurality of layers including a piezoelectric element layer, wherein
    at least one surface of electrodes that forms a pair of adjacent layers among the layers, is made of metal including a plurality of needle-like structures, the pair of adjacent layers being made of conductive material and facing each other.

12. An electrode structure of an ultrasonic transducer element including a plurality of layers including a piezoelectric element layer, wherein
    at least one surface of surfaces that forms a pair of adjacent layers among the plurality of layers is provided with an electrode made of metal including a plurality of needle-like structures, the pair of adjacent layers being made of conductive material, and facing each other.

* * * * *